United States Patent
Wang

(10) Patent No.: US 6,616,943 B2
(45) Date of Patent: Sep. 9, 2003

(54) COMPOSITION COMPRISING WENGUANGUO EXTRACTS AND METHODS FOR PREPARING SAME

(75) Inventor: Yun Wang, Dunedin (NZ)

(73) Assignee: Fountain Silver Limited, Kowloon (HK)

( * ) Notice: Subject to any disclaimer, the term of this patent is extended or adjusted under 35 U.S.C. 154(b) by 0 days.

(21) Appl. No.: 09/944,805

(22) Filed: Aug. 31, 2001

(65) Prior Publication Data

US 2003/0091669 A1 May 15, 2003

(51) Int. Cl.[7] .................................................. A61K 9/48
(52) U.S. Cl. ........................ 424/451; 424/464; 424/489; 424/725; 424/776; 424/777
(58) Field of Search ................................ 424/725, 776, 424/777, 451, 464, 489

(56) References Cited

U.S. PATENT DOCUMENTS 6,197,306 B1 * 3/2001 Murali ..................... 424/195.1

FOREIGN PATENT DOCUMENTS

CN 1092992 A * 10/1994

OTHER PUBLICATIONS

Chen Y et al., Chem. Pharm. Bull. 33(1): 127–134, 1985 [Exhibit 3].

* cited by examiner

Primary Examiner—Thurman K. Page
Assistant Examiner—Liliana Di Nola-Baron
(74) Attorney, Agent, or Firm—Albert Wai-Kit Chan; Mark Elkins

(57) ABSTRACT

This invention provides a composition comprising extracts from the husk of Wenguanguo and a process of producing the combined extract comprising the following steps: extracting Wenguanguo husks with an organic solvent to form an organic extract; removing the organic solvent from the extract to form aqueous extracts; and drying and sterilizing the aqueous extracts to form the combined extracts. The extracts can be used to make medicines or health foods for preventing cerebral aging, improving memory, improving cerebral functions and curing enuresis, frequent micturition, urinary incontinence, dementia, weak intelligence and Alzheimer's disease and other diseases caused by cerebral dysfunction. The combined extracts contain saponin, saccharides, proteins and others.

8 Claims, 1 Drawing Sheet

Saponin Structure A, B, C, D

COMPOSITION COMPRISING WENGUANGUO EXTRACTS AND METHODS FOR PREPARING SAME

Figure 1:
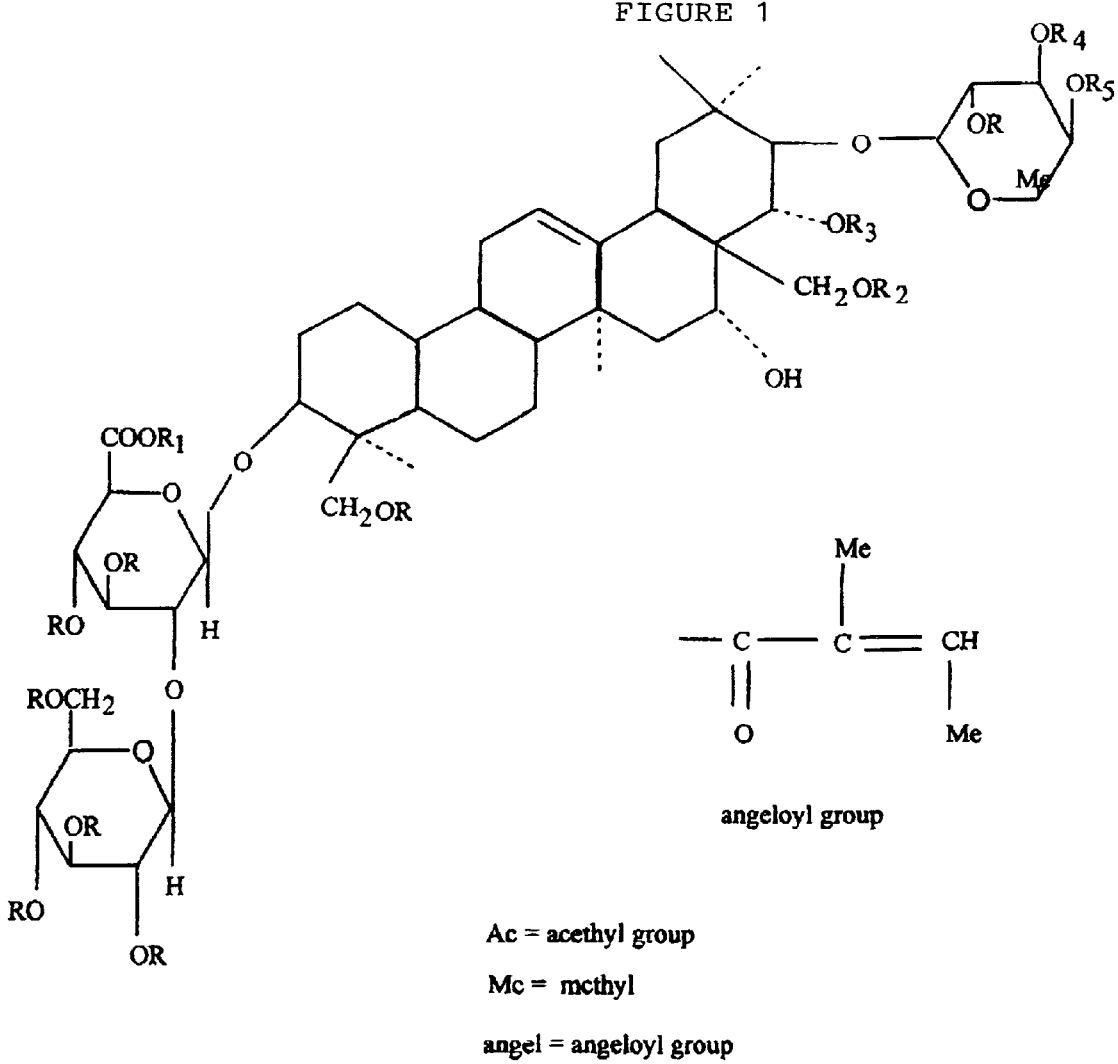

Throughout this application, various references are referred to. Disclosures of these publications in their entireties are hereby incorporated by reference into this application to more fully describe the state of the art to which this invention pertains.

FIELD OF THE INVENTION

This invention relates to combined extracts and a crude saponin extract from a plant called Wenguanguo and methods of their preparation. The extracts can be used to make medicines or health foods for preventing cerebral aging, improving cerebral functions and curing enuresis, frequent micturition, urinary incontinence, dementia, weak intelligence and Alzheimer's disease other diseases caused by cerebral dysfunctions.

BACKGROUND OF THE INVENTION

In recent years there has been a growing interest in finding novel extracts from plants to make medicines or health foods for preventing and curing diseases or improving human health. Using medicinal herbal plants for treating diseases or improving human health has long been a tradition in China. The Chinese herbal plants have been excellent resources for developing these extracts. More and more novel plant extracts have been developed from Chinese medicinal plants, such as Ginseng, Ginkgo, Chongcao and etc (Zhang TCH et al., 2000).

Wenguanguo is a plant that is endemic to China (Zhu YCH et al, 1989), and it has been used as a folk remedy for curing enuresis for a long time (Chen Y et al., 1984; Zhu YCH et al, 1989). However, Wenguanguo has not been fully explored as a potential medicine or health food for preventing cerebral dysfunction and improving cerebral function. In Chinese patents CN1092991A and CN1092992A, a kernel powder made from Wenguanguo seed kernel has been studied and a medicine called Yiniaoting has been developed for the treatment of enuresis. However, the content of the bioactive ingredients Saponin in Yiniaoting is very low and therefore, large dosages are inevitable for effective treatment. Furthermore, the process of making Yiniaoting from Wenguanguo seeds is arduous, costly and complicated. In this invention two novel extracts from the Wenguanguo husks are provided and methods of producing them are developed. These extracts offer improved medicinal effects and lower processing costs.

SUMMARY OF THE INVENTION

This invention relates to combined extracts and a crude saponin extract from Wenguanguo husks and methods of their preparation. Both husk extracts have a higher saponin concentration (30–32% or more) compared with the kernel powder (2–4%) and its extracts (10–19%) in previous work. Therefore, the dosage of medicines made from the husk extracts is only 3 capsules or pills per day, compared with kernel powder, which is 18 per day. It is much easier for patients to take, children in particular, and it also greatly reduces patients' costs.

This invention provides a process of producing the two husk extracts. The cost of producing the two extracts from the husks is much lower due to the much lower cost of purchasing husks and simplified methods.

This invention provides a composition comprising extracts from the husk of Wenguanguo.

The invention also provides a process of producing the combined extract comprises following steps: a) extracting Wenguanguo husks with an organic solvent to form an organic extract; b) removing the organic solvent from the extract to form aqueous extracts; and c) drying and sterilizing the aqueous extracts to form the combined extracts.

This invention provides a crude saponin extract from Wenguanguo husks for preventing cerebral aging, improving cerebral functions and curing enuresis, frequent micturition, urinary incontinence, dementia, weak intelligence and Alzheimer's disease and other diseases caused by cerebral dysfunctions.

This invention also provides a process of production of crude saponin extract from Wenguanguo husks comprising the steps of:

a) extracting the Wenguanguo husks by alcohol or other organic solvent (methanol and others) at ratio of 1:2 for 4–5 times, 20–35 hours for each time to form alcohol extracts;

b) collecting and refluxing the alcohol extracts for 2–3 times at 80° C. to form second extracts;

c) collecting the second extracts and removing said solvent from the extracts to form a combined extract;

d) resolving the combined extracts in water to from an aqueous solution;

e) extracting the solution by n-butanol to form n-butanol extracts;

f) chromatographing the n-butanol extracts to form crude saponin.

DETAILED DESCRIPTION OF THE FIGURES

FIG. 1. Structure of Saponin

DETAILED DESCRIPTION OF THE INVENTION

This invention provides a composition comprising extracts from Wenguanguo. This composition may be used for preventing cerebral aging, improving memory, improving cerebral functions and curing enuresis, frequent micturition, urinary incontinence, dementia, weak intelligence and Alzheimer's disease and other diseases caused by cerebral dysfunctions.

In an embodiment, the above composition are combined extracts from Wenguanguo husks including stems of fruits. The combined extracts may be alcohol extracts. The alcohol includes, but it is not limited to ethanol, methanol and other organic solvents such as light petroleum, ether. The combined extracts contains saponins and other compounds. In an embodiment, the above composition comprises saponin 30–32%, saccharides 10–17%, protein 7–11%, water 6–9%, fat 1–4% and others 20–29%.

The invention also provides a process of producing the combined extracts comprises following steps: (a) extracting Wenguanguo husks with an organic solvent to form an organic extract, wherein the solvent is alcohol; (b) removing the organic solvent from the extracts to form aqueous extracts; and drying and sterilizing the aqueous extracts to form the combined extracts.

In an embodiment, the above process further comprises milling or grinding said Wenguanguo husks prior to the extraction step. In another embodiment the above process further comprises drying said Wenguanguo husks prior to said milling step. In still another embodiment, the above process further comprises selecting and cleaning said Wenguanguo husks prior to said drying step. In a further embodiment, the above process comprises harvesting said Wenguanguo husks prior to the cleaning and selecting step.

In a separate embodiment, the above process uses Wenguanguo fruits which are harvested from August to October from Wenguanguo trees. In an embodiment of the alcohol extraction the ratio of the Wenguanguo husks and the alcohol is 1:2. In another embodiment, the extraction is performed 4–5 times at room temperature. In a further embodiment, the extraction is carried out for 20–35 hours for each time. Alcohol extracts are filtered and combined in a still further embodiment. The combined extracts are refluxed at 80° C. for 2–3 times. Medicines or health foods are produced from said combined extracts for treating enuresis and other diseases caused by cerebral dysfunctions and improving cerebral functions. The said medicines or health foods are made in capsule, pill, powder, liquid or other forms known to an ordinary skilled artisan.

This invention also provides a crude saponin extract from Wenguanguo husks for preventing cerebral aging, improving cerebral functions and curing enuresis, frequent micturition, urinary incontinence, dementia, weak intelligence and Alzheimer's disease and other diseases caused by cerebral dysfunctions.

This invention also provides a process of production of the crude saponin extract from said Wenguanguo husks comprises the steps of: (a) extracting the Wenguanguo husks by alcohol or other organic solvent (methanol and others) at ratio of 1:2 for 4–5 times, 20–35 hours for each time to form alcohol extracts; (b) collecting and refluxing said alcohol extracts for 2–3 times at 80° C. to form second extracts (Chen Y et al., 1984); (c) collecting said second extracts and remove said solvent from them to form a combined extracts; (d) resolving the combined extracts in water to form an aqueous solution; (e) extracting the solution by n-butanol to form n-butanol extracts; and (f) chromatographing the n-butanol extracts to form the crude saponin.

In a separate embodiment, this invention provides a process which comprises producing medicines or health foods from said crude saponin for treating enuresis and other diseases caused by cerebral dysfunctions and improving cerebral functions.

In yet another embodiment, this invention provides the above compound wherein said medicines or health foods are made in capsule, pill, powder, liquid and other forms.

Finally, this invention provides the compounds above further comprising Vitamin B, Vitamin D, Vitamin K, antioxidant, cordyceps, gingko, or its extract, ginseng or its extract, Echinacea or its extract, Huperzine A, folic acid, amino acids, creatine, fiber supplement, or any combination thereof.

Medicines or health foods are produced from said crude saponin for treating enuresis and other diseases caused by cerebral dysfunctions and improving cerebral functions. Said medicines or health foods are made in capsule, pill, powder, liquid and other forms. The medicines or health foods further comprise Vitamin B, Vitamin D, K, an antioxidant, cordyceps, gingko, or its extract, ginseng, or its extract, Echinacea, or its extract, Huperzine A, folic acid, amino acids, creatine, fiber supplement or a combination thereof.

This invention relates to two novel extracts: a combined extract and a crude saponin extract from Weguanguo husks and methods of their preparation. The extracts can be used to make medicines or health foods for preventing cerebral aging, improving cerebral functions and curing enuresis, frequent micturition, urinary incontinence, dementia, weak intelligence, and Alzheimer's disease and other diseases caused by cerebral dysfunction.

Wenguanguo is a species of Sapindaceae family. Its scientific name is *Xanthoceras sorbifolia* Bunge. Wenguanguo is one common Chinese name, others are Wenguanwu, Wenguangua, Wenguanshu and Xilacedeng (Wenguanguo's Mongolian herb name). This plant is a small tree up to 8 m in height. It features odd pinnately compound leaf, raceme with white flowers, capsules with thick and woody husks, and 1–8 black seeds. It is endemic to Northern China and has been cultivated in China for ages. The seed contains oil, up to 50% or more of which is edible. The stem and branches are Chinese herbs recorded in the Chinese materia medica specified in pharmacopoeia of The People's Republic China. The seeds have been used as a folk medicinal herb for curing enuresis for ages.

In recent years research showed the extracts from Wenguanguo seeds could yield potential remedies for treating cerebral diseases. A new medicine for curing enuresis has been developed from the kernel powders of Wenguanguo seeds.

This invention provides a novel extract from Wenguanguo husks and methods of their preparation. The combined extracts have improved medicinal properties compared with kernel powders and extracts from Wenguanguo seeds due to their higher saponin concentration (Table 1).

TABLE 1

| Comparison of contents and components of extracts from husks and seeds | | | | | |
|---|---|---|---|---|---|
| | Saponin | Saccharides | Protein | Water | Fat | Others |
| A | 30–32 | 15–25 | 8–14 | 7–10 | 1–4 | — |
| B | 10–19 | 20–30 | 15–20 | 10–15 | 1–10 | — |
| C | 2–4 | — | 55–65 | 7–16 | 1–10 | — |

A: combined extracts from husks; B: extracts from seed kernel powder; C: seed kernel powders.

This invention provides a process of producing the combined extracts from the husks. The cost of producing the extracts from the husks is much lower due to the much lower cost of husks and a simple method for extraction. The price of husks is only 25% of that of the seeds.

The process of producing the extracts from seeds includes 10 steps: collecting and drying the seeds; removing shells from seeds to get the kernels; pressing the kernels for pre-removing oils from the kernels to form the kernel bricks; drying and milling the bricks to get the kernel powder; removing the oils from the powder by alcohol extraction; removing the alcohol from the powder; drying and milling the powder again; extracting the powder by ethanol to form ethanol extracts; removing the ethanol to form the extracts and then sterilizing the extracts to form final products. But the process of producing the husk extracts includes only 5 steps as follows:

1. collect and dry the husks;
2. mill said dried husks to form husk powder;
3. extract said husks powder with alcohol to form alcohol extracts;
4. remove the alcohol from said alcohol extracts to form aqueous extracts;
5. dry and sterilize said aqueous extracts to form the combined extracts.

Therefore, the cost of producing the combined extracts from husks with a concentration of 1 kg saponin is approximately only 40% of the cost from seeds.

The combined extracts can be used in different forms, such as capsules and pills as the seed extracts do. However, the dosages of medicines made from the combined extracts are 3 capsules or pills/day compared with 18 capsules or pills/day from "Yiniaoting" due to the higher saponin concentration. Therefore, it is much easier to be taken by patients, by children in particular, and also greatly reduces patients' costs.

This invention also provides a crude saponin extract from Wenguanguo husks (including fruit stems) and a process of their preparation. The crude saponin extracts is a further extract from the combined extracts, which is potentially a better remedy for preventing cerebral aging, improving cerebral function and curing enuresis, frequent micturition, urinary incontinence, dementia, weak intelligence and Alzheimer's disease and other diseases caused by cerebral dysfunctions. The main component in the extracts is saponin (over 50%). The process of producing the crude saponin extracts includes the following steps:

1. Extract the husks powder by alcohol or other organic solvent (methanol and others) at ratio of 1:2 for 4–5 times, 20–35 hours for each time to form alcohol extracts;
2. Collect and reflux said alcohol extracts for 23 times at 80° C. to form second extracts;
3. Collect said second extracts and remove said alcohol from them to form combined extracts;
4. Resolve said combined extracts in water to form a aqueous solution;
5. Extract said solution by n-butanol to form a n-butanol extracts;
6. Chromatograph said n-butanol extracts to form the crude saponin extracts.

The crude saponin extracts can be used to make medicines or health foods in different forms for preventing cerebral aging, improving cerebral function and curing enuresis, frequent micturition, urinary incontinence, dementia, weak intelligence and Alzheimer's disease and other diseases caused by cerebral dysfunction.

The two novel extracts provided by this invention are developed from a Chinese folk herb, Wenguanguo. They are the best remedy for curing enuresis without any side effects on the earth and could be a potential for preventing cerebral aging, improving cerebral function and curing enuresis, frequent micturition, urinary incontinence, dementia, weak intelligence and Alzheimer's disease and other diseases caused by cerebral dysfunction. The processes for preparing them are simple and low in cost.

This invention is further illustrated in the following examples.

EXAMPLE 1

A sample illustrating the method of producing a combined extract from husks.

1. Collect, dry and mill Wenguanguo husks to form 10 kg of husks powder;
2. Extract said husks powder by 20 L of ethanol for 4–5 times, 20–35 hour for each time;
3. Collect and reflux the ethanol extracts at for 2–3 times at 80° C. to form second extracts;
4. Collect said second extracts and remove ethanol them to form aqueous extracts;
5. Dry and sterilize said aqueous extracts to from 140.5 g of combined extracts.

Components and contents of the extracts are as follows:

| Saponin | Saccharides | Protein | Water | Fat | Others |
|---------|-------------|---------|-------|-----|--------|
| 31.3 | 17.2 | 11.6 | 9.4 | 3.9 | 26.6 |

EXAMPLE 2

Fifty g of the combined extracts from the example 1 is softened with ethanol. The softened extracts are then sieved and granulated. The granulated extracts are capsulized to form 250 capsules. Ten capsules are packed in a bottle. The child's dosage for treating enuresis is one capsule three times a day. One to three courses of treatment are needed and each lasts 15 days.

EXAMPLE 3

Fifty g of the combined extracts from Example 1 is softened with ethanol. The softened extracts are then sieved and powdered. The powder is mixed well with 450 g glucose, and then granulated. The granules are packed in small bags with 2 g of each. Dosage to treat child enuresis is 3 times/day, one bag for each time. One to three courses of the treatment is needed and each lasts 15 days.

EXAMPLE 4

Forty g of the combined extracts from Example 1 is softened with ethanol. The softened extracts are then sieved and powdered. The powders are mixed with 0.8 g starch, 0.4 g talcum powder and a little ethanol and then are pilled to form 250 pills. The pills can be used to treat enuresis and other disease caused by cerebral dysfunction. The dosage for treating child enuresis is 3 times per day, one pill each time. One to three courses of the treatment are needed, and each lasts 15 days.

EXAMPLE 5

A sample illustrating the method of producing the crude saponin from husks.

1. Collect, dry and mill Wenguanguo husks to form 20 kg of husks powder;
2. Extract said husks powder by 40 L of ethanol for 4–5 times, 20–35 hour for each time;
3. Collect and reflux the ethanol extracts at for 2–3 times at 80° C. to form second extracts;
4. Collect said second extracts and remove ethanol them to form aqueous extracts;
5. Dry and sterilize said aqueous extracts to from 281.5 g of combined extracts;
6. Resolve said combined extracts in water to form an aqueous solution;
7. Extract said solution by n-butanol to form a n-butanol extracts;
8. Fractionate said n-butanol extracts by droplet counter-current chromatography (d.c.c) using a $CHCl_3$—MeOH—$H_2O$ (35:65:40) solvent system (upper layer as the mobile phase, lower layer as the stationary phase).
9. Collect and combine said saponin fractions.
10. Remove the solvents by evaporation gave 21.6 g crude saponins.

EXAMPLE 6

9.0 g the crude saponin from example 5 mixed with starch, talcum powder and a little of ethanol are pilled to form 250 pills. The pills are sterilized and packed for treating enuresis and other disease caused by cerebral dysfunctions. The dosage for treating child enuresis is 3 times a day, one pill each time. One to three courses of the treatment are needed, and each lasts 15 days.

EXAMPLE 7

9.0 g the crude saponin from Example 5 is encapsulated to form 250 of capsules. Each of 10 capsules is packed in a bottle for treating enuresis and other disease caused by cerebral dysfunction. The dosage for treating child enuresis is 3 times for a day, one capsule each time. One to three courses of the treatment are needed, and each lasts 15 days.
References 1. Chen Y et al., Chem. Pharm. Bull. 33(1): 127–134, 1985
2. Zhang TCH et al., Proceedings of national conference on medicinal plants, Dalian, China, 2000.
3. Zhu YCH et al., Platae medicinales Chinae boreali-orientalis, 710–711, Heilongjiang Science & Technology Publishing House, 1989.
4. Lu Guiyuan and Wang Yitao, Study of development new Chinese medicines, 286–292, People Health Publish House, Beijing 1998.

What is claimed is:

1. A composition from the husk of Wenguanguo comprising saponin 30–32%, saccharides 15–25%, protein 8–14%, water 7–10%, and fat 1–4%.

2. A composition from the husk of Wenguanguo comprising at least 30% saponin, saccharides 15–25%, protein 8–14%, water 7–10%, and fat 1–4%.

3. A medicine or health food comprising the compostion of claim 1 in capsule, pill, powder, or liquid forms.

4. A medicine or health food comprising the composition of claim 2 in capsule, pill, powder, or liquid forms.

5. A medicine or health food comprising the composition of claim 1, further comprising Vitamin B, Vitamin D, Vitamin K, antioxidant, cordyceps or its extract, gingko or its extract, ginseng or its extract, Echinacea or its extract, Huperzine A, folic acid, amino acids, creatine, fiber supplement, or any combination thereof.

6. The medicine or health food or claim 5 in capsule, pill, powder, or liquid forms.

7. A medicine or health food comprising the composition of claim 2, further comprising Vitamin B, Vitamin D, Vitamin K, antioxidant, cordyceps or its extract, gingko or its extract, ginseng or its extract, Echinacea or its extract, Huperzine A, folic acid, amino acids, creatine, fiber supplement, or any combination thereof.

8. The medicine or health food of claim 7 in capsule, pill, powder, or liquid forms.

* * * * *